United States Patent
Bar-Tal et al.

(10) Patent No.: US 11,109,792 B2
(45) Date of Patent: Sep. 7, 2021

(54) SIGNAL COLOR MORPHOLOGY

(71) Applicant: Biosense Webster (Israel) Ltd., Yokneam (IL)

(72) Inventors: Meir Bar-Tal, Haifa (IL); Moshe Ingel, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 229 days.

(21) Appl. No.: 15/885,325

(22) Filed: Jan. 31, 2018

(65) Prior Publication Data
US 2019/0231209 A1  Aug. 1, 2019

(51) Int. Cl.
| | |
|---|---|
| *A61B 5/349* | (2021.01) |
| *G09G 5/02* | (2006.01) |
| *G06F 3/147* | (2006.01) |
| *A61B 5/25* | (2021.01) |
| *A61B 5/322* | (2021.01) |
| *A61B 5/339* | (2021.01) |
| *A61B 5/316* | (2021.01) |
| *A61B 5/333* | (2021.01) |

(52) U.S. Cl.
CPC ............... *A61B 5/349* (2021.01); *A61B 5/25* (2021.01); *A61B 5/322* (2021.01); *A61B 5/339* (2021.01); *G06F 3/147* (2013.01); *G09G 5/02* (2013.01); *A61B 5/316* (2021.01); *A61B 5/333* (2021.01); *G09G 2340/045* (2013.01); *G09G 2380/08* (2013.01)

(58) Field of Classification Search
CPC ..... A61B 5/0452; A61B 5/0408; A61B 5/044; A61B 5/04023; A61B 5/04012
USPC .......................................................... 600/523
See application file for complete search history.

(56) References Cited

U.S. PATENT DOCUMENTS

| | | | |
|---|---|---|---|
| 5,741,887 A | 4/1998 | Morita et al. | |
| 5,782,773 A | 7/1998 | Kuo et al. | |
| 2004/0054294 A1* | 3/2004 | Ramseth | A61B 5/044 |
| | | | 600/509 |
| 2006/0085049 A1 | 4/2006 | Cory et al. | |
| 2008/0137927 A1 | 6/2008 | Altmann et al. | |
| 2010/0036227 A1 | 2/2010 | Cox et al. | |
| 2011/0021936 A1* | 1/2011 | Luo | A61B 5/044 |
| | | | 600/523 |
| 2013/0123773 A1 | 5/2013 | Schwartz | |
| 2015/0112218 A1 | 4/2015 | Shani et al. | |
| 2015/0141862 A1* | 5/2015 | Montambeau | A61B 5/748 |
| | | | 600/523 |

* cited by examiner

*Primary Examiner* — Amanda K Hulbert
*Assistant Examiner* — Philip C Edwards
(74) *Attorney, Agent, or Firm* — Volpe Koenig

(57) ABSTRACT

The present system allows for the physician to change the relative height of the signal to allow for examination of details of the signals, while maintaining an ability to interpret signal voltage levels absolutely based on color or other secondary mechanism beyond signal height. The disclosed system and method provide for faster and more accurate analysis based upon the color of the signal. The signal height may change, such as to view, display, or examine details of the signal, while the colors of the display do not. The color scale of the signal provides an absolute scaling of the signal regardless of the displayed height.

20 Claims, 4 Drawing Sheets
(2 of 4 Drawing Sheet(s) Filed in Color)

SIGNAL COLOR MORPHOLOGY

FIELD OF INVENTION

The present invention relates to presentation of signals for interpretation, and more particularly to presentation of signals for interpretation by medical personnel.

BACKGROUND

Medical personnel often rely on the interpretation of signal voltage levels to understand the morphology of an organ, tissue or other biological structure. Medical personnel interpret the signal voltage based on relative height. Currently, each signal voltage can be changed independently from the other signal voltages. The result is that the medical personnel cannot rely on the signal height to interpret the morphology. Therefore, a need exists to provide physicians a way to interpret the signal voltage based on relative height.

SUMMARY

The present system allows for the physician to change the relative height of the signal to allow for examination of details of the signals, while maintaining an ability to interpret signal voltage levels absolutely based on color or other secondary mechanism beyond signal height. The disclosed system and method provide for faster and more accurate analysis based upon the color of the signal. The signal height may change, such as to view, display, or examine details of the signal, while the colors of the display do not. The color scale of the signal provides an absolute scaling of the signal regardless of the displayed height.

A system and method of for displaying measured signal for a device is disclosed. The system and method include monitoring signals in the device, displaying signals on a display, the signals being at least a subset of the monitored signals, controlling a first voltage display level to provide display of at least one displayed measured signals with a height designed to examine details of the measured signal, and providing a second scale to the entirety of the signals displayed independent of the first voltage display level.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A more detailed understanding may be had from the following description, given by way of example in conjunction with the accompanying drawings wherein.

DETAILED DESCRIPTION

Figure 1:
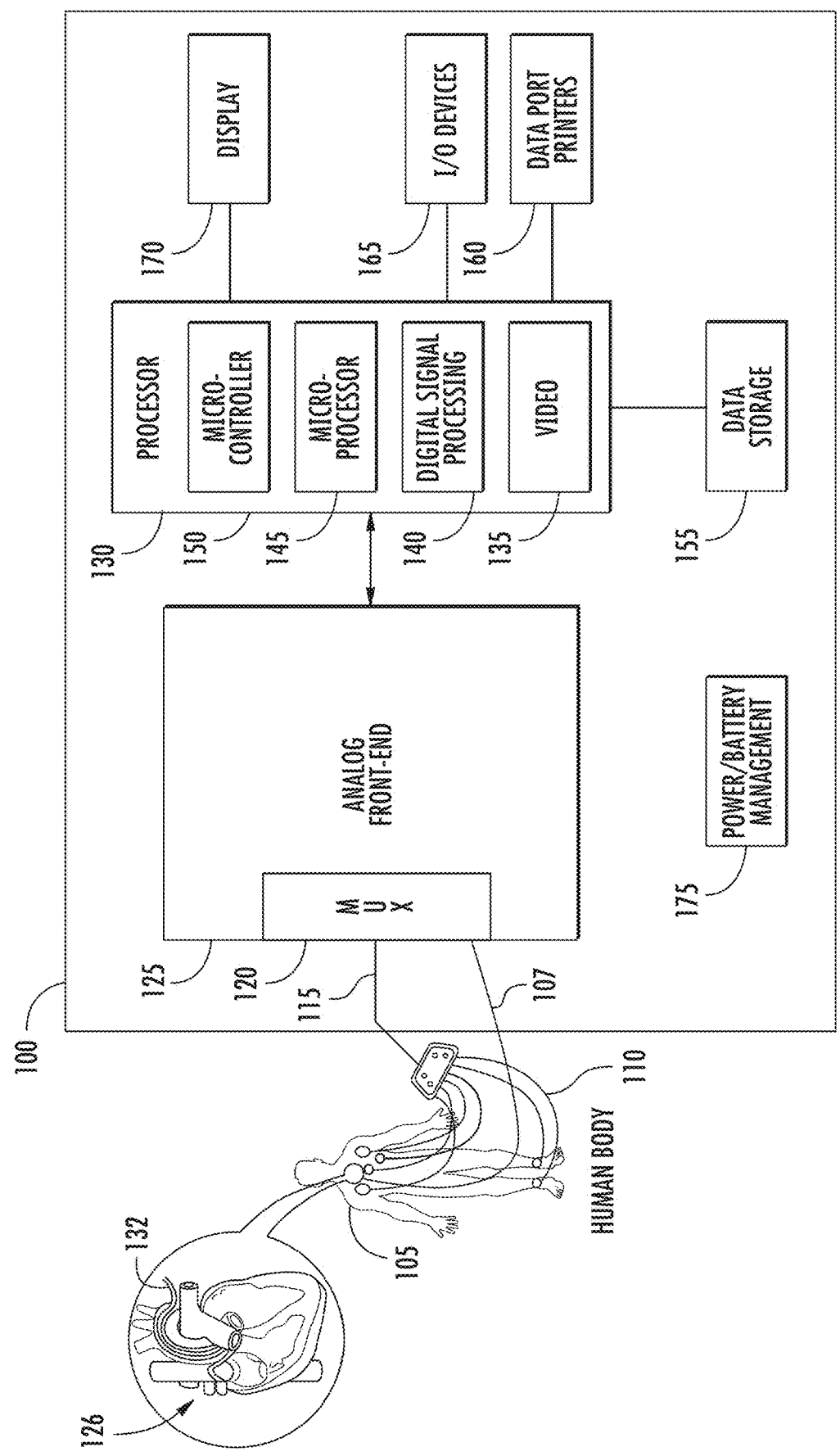
FIG. 1 illustrates a block diagram of a device that may be used in conjunction with or provide feedback to the system described herein.

In the following description, numerous specific details are set forth, such as particular structures, components, materials, dimensions, processing steps, and techniques, in order to provide a thorough understanding of the present embodiments. However, it will be appreciated by one of ordinary skill of the art that the embodiments may be practiced without these specific details. In other instances, well-known structures or processing steps have not been described in detail in order to avoid obscuring the embodiments. It will be understood that when an element such as a layer, region, or substrate is referred to as being "on" or "over" another element, it can be directly on the other element or intervening elements may also be present. In contrast, when an element is referred to as being "directly on" or "directly" over another element, there are no intervening elements present. It will also be understood that when an element is referred to as being "beneath," "below," or "under" another element, it can be directly beneath or under the other element, or intervening elements may be present. In contrast, when an element is referred to as being "directly beneath" or "directly under" another element, there are no intervening elements present.

In the interest of not obscuring the presentation of embodiments in the following detailed description, some structures, components, materials, dimensions, processing steps, and techniques that are known in the art may have been combined together for presentation and for illustration purposes and in some instances may have not been described in detail. In other instances, some structures, components, materials, dimensions, processing steps and techniques that are known in the art may not be described at all. It should be understood that the following description is rather focused on the distinctive features or elements of various embodiments described herein.

Cardiac electrophysiology is the science of elucidating, diagnosing, and treating the electrical activities of the heart. One medical system that is used in this area is the CARTO system. In certain procedures, cardiac electrophysiology may be used to treat arrhythmias by ablating tissue surrounding the heart that is either the source of unwanted beats or conducts unwanted signals. After treatment, the ablation results in a denaturing of the tissue preventing the tissue from conducting the unwanted signals or beats.

Electrocardiography, referred to herein as ECG, and may also be referred to as EKG, is the process of recording the electrical activity of the heart over a period of time using electrodes placed on the skin, or inside the heart using a specialized catheter (i.e. intracardiac ECG). These electrodes detect the small electrical changes that arise from the cardiac muscle's electro-physiologic pattern of depolarizing during each heartbeat. ECGs are commonly or routinely performed cardiology tests. The machine used in the test is an electrocardiograph and the initial output is an electrocardiogram. For the sake of brevity, electrocardiography, electrocardiograph, and electrocardiogram are all referred to herein as ECG, and may also be referred to as EKG.

An intracardiac electrogram (ICEG) is an ECG with some added intracardiac leads (i.e., inside the heart). Such an ICEG may be utilized in combination with, or in the alternative to, a conventional 12-lead ECG. In a conventional 12-lead ECG, 10 electrodes are placed on the patient's limbs and on the surface of the chest. The overall magnitude of the electrical potential of the heart is then measured from 12 different angles ("leads") and is recorded over a period of time. The procedure duration may vary from tens of minutes to several hours. During each procedure, there are usually several dozens of ablation sessions, each of which may last several seconds up to approximately 1 minute, for example. By way of example, a conventional 12-lead ECG may be performed over a period of time, such as 10 seconds, for example. In this way, the overall magnitude and direction of the electrical depolarization of the heart is captured at each moment throughout the cardiac cycle. A graph of voltage versus time produced by this medical procedure is referred to as an electrocardiogram.

During each heartbeat, a healthy heart has an orderly progression of depolarization. This orderly pattern of depolarization gives rise to the characteristic ECG tracing. To the trained clinician, an ECG conveys a large amount of information about the structure of the heart and the function of its electrical conduction system. Among other things, an ECG can be used to measure the rate and rhythm of heartbeats, the size and position of the heart chambers, the presence of any damage to the muscle cells or conduction system of the heart, the effects of cardiac drugs, and the function of implanted pacemakers. Interpretation of the ECG is fundamentally about understanding the electrical conduction system of the heart. Normal conduction starts and propagates in a predictable pattern, and deviation from this pattern can be a normal variation or be pathological.

As set forth above, cardiac electrophysiology is the science of diagnosing and treating the electrical activities of the heart using, among other techniques, the ECG. The term is usually used to describe studies of such phenomena by invasive (intracardiac) catheter recording of spontaneous activity as well as of cardiac responses to programmed electrical stimulation (PES). These studies are performed to assess complex arrhythmias, elucidate symptoms, evaluate abnormal electrocardiograms, assess risk of developing arrhythmias in the future, and design treatment. Therapeutic methods include ablations. Ablation generally refers to the removal, killing or scarring of biological tissue, such as to alter the contraction patterns, usually by surgery, and may include methods of ablating aberrant tissue from within the body via minimally invasive procedures. In cardiac electrophysiology procedures, the dysfunctional tissue may be ablated using heat generated from alternating electric current at radio frequencies in the range of 350-500 kHz. As part of the ablation procedure, the ablation electrode, used in ablating the tissue, may be monitored for temperature as compared to a maximum or target temperature and once the temperature is reached, power may be switched to another of the electrode within the multi-electrode system.

FIG. 1 illustrates a block diagram of a device 100 that may be used in conjunction with or provide feedback to the system described herein. Device 100 may take the form of an ECG. Device 100 includes a series of leads 110 that taper into a single multiplexed input 115. The series of leads 110 may be placed on a human test subject 105. Additional leads 107, which may be included with series of leads 110, or separate therefrom (as shown) may be intracardiac leads 107.

Intracardiac leads 107 may be used for diagnostic or therapeutic treatment, such as for mapping electrical potentials in a heart 126 of a patient 105. Alternatively, intracardiac leads 107 may be used, mutatis mutandis, for other therapeutic and/or diagnostic purposes in the heart or in other body organs.

Intracardiac leads 107 may be inserted in the vascular system of the patient 105 so that a distal end 132 of the leads 107 enters a chamber of the patient's heart 126. Although FIG. 1 shows a single lead 107 with a single location sensor, embodiments of the present invention may utilize probes with more than one location sensor.

The signals on the series of leads 110 are input into an analog front-end 125 via an input multiplexor 120. The analog front-end 125 provides to and is controlled by a processor 130. Processor 130 may include, as shown, a video controller 135, digital signal processor 140, a microprocessor 145, and a micro controller 150. Processor 130 is coupled to a data storage 155. Data ports and printers 160 may be coupled to processor 130. Other input/output devices 165 may be coupled to processor 130. A display 170 may be used to provide output of the signals of the ECG. A power/battery management system 175 may be included to provide power for device 100 to operate.

Series of leads 110 includes both the generally used forms of electrodes and leads. One or more of the series of leads 110 may include an ablation electrode the details of which will be described in more detail herein. The series of leads 110 may include a conductive pad in contact with the body 105 that makes an electrical circuit with the electrocardiograph. On a standard 12-lead ECG there are only 10 leads 110. Series of leads 110 may be grouped into three sets: limb, augmented limb, and precordial. Generally, the 12-lead ECG has a total of three limb leads and three augmented limb leads arranged like spokes of a wheel in the coronal plane (vertical) and six precordial leads that lie on the perpendicular transverse plane (horizontal).

Analog front-end 125 receives the signals from the series of leads 110 and performs analog processing, such as filtering, of the signals.

Data storage 155 is any device that records information. Data storage may provide a storage medium for the signals includes within device 100 and a place for calculations of processor 130 to be stored.

Microprocessor 145 may be a computer processor which incorporates the functions of a computer's central processing unit (CPU) on a single integrated circuit (IC), or a few integrated circuits. Microprocessor 145 may be a multipurpose, clock driven, register based, programmable electronic device which accepts digital or binary data as input, processes it according to instructions stored in its memory or data storage 155, and provides results as output. Microprocessor 145 contains both combinational logic and sequential digital logic.

Micro controller 150 may be one or more small computers on a single integrated circuit. Micro controller 160 may contain one or more CPUs along with memory and programmable input/output peripherals. Program memory in the form of Ferroelectric RAM, NOR flash or OTP ROM is also often included on chip, as well as a small amount of RAM. Microcontrollers are designed for embedded applications, in contrast to the microprocessors used in personal computers or other general purpose applications consisting of various discrete chips.

Digital signal processor (DSP) 140 may perform digital signal processing to perform a wide variety of signal processing operations. The signals processed in this manner are a sequence of numbers that represent samples of a continuous variable in a domain such as time, space, or frequency. Digital signal processing can involve linear or nonlinear operations. Nonlinear signal processing is closely related to nonlinear system identification and can be implemented in the time, frequency, and spatio-temporal domains. The application of digital computation to signal processing allows for many advantages over analog processing in many applications, such as error detection and correction in transmission as well as data compression. DSP is applicable to both streaming data and static (stored) data.

Medical personnel often rely on the interpretation of signal voltage levels to understand the morphology of an organ, tissue or other biological structure. Medical personnel interpret the signal voltage based on relative height. Currently, each signal voltage can be changed independently from the other signal voltages. Often the signal height may be changed from one signal to another in order to examiner the signal or to observe a desired feature that is visible with increased magnification of the signal, for example. The result is that the medical personnel cannot rely on the signal height to interpret the morphology across different signals.

The interpretation of signal voltage levels for organ and tissue morphology is often inaccurate when based upon the relative height of the signal voltage. The present system allows for the physician to change the relative height of the signal to allow for examination of details of the signals, while maintaining an ability to interpret signal voltage levels absolutely based on color or other secondary mechanism beyond signal height. The disclosed system and method provide for faster and more accurate analysis based upon the color of the signal. The signal height may change, such as to view, display, or examine details of the signal, while the colors of the display do not. The color scale of the signal provides an absolute scaling of the signal regardless of the displayed height.

Figure 2:
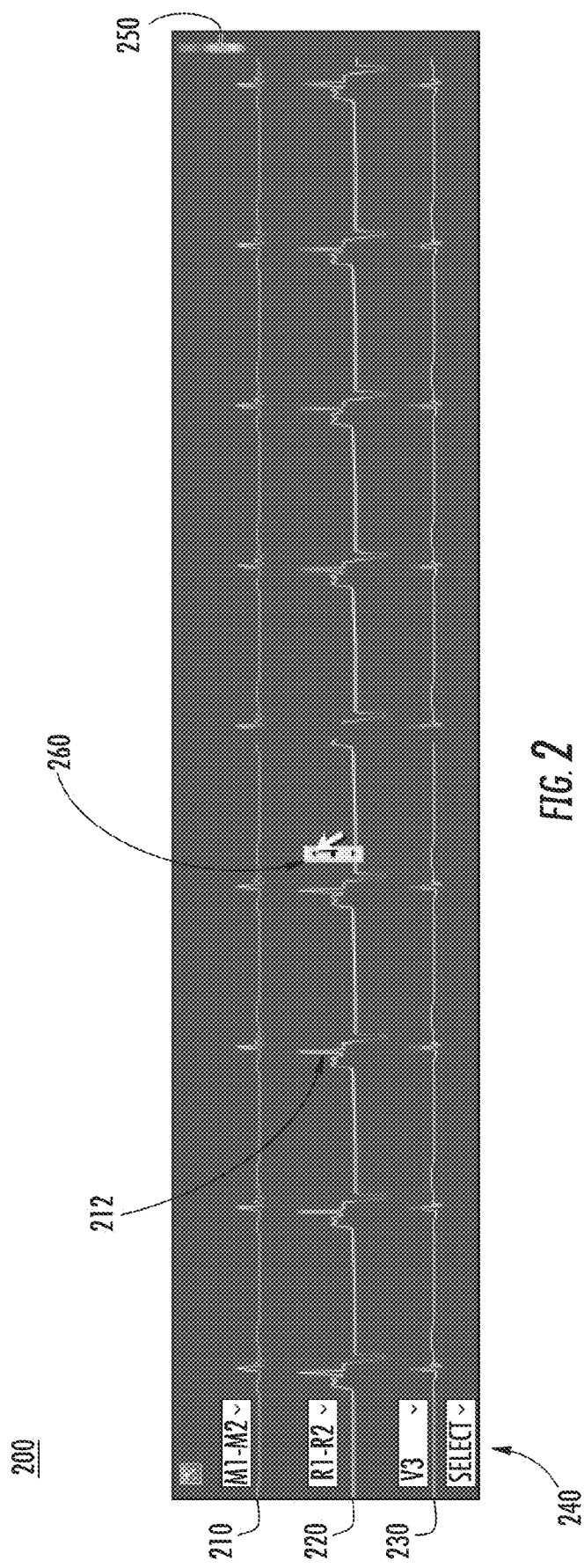
FIG. 2 illustrates several plots of the signal voltages of the device of FIG. 2.

Referring now to FIG. 2, there is illustrated of several plots 200 of the signal voltages, which may be presented on display 170 of FIG. 1. A first plot 210 illustrates the signal voltage across M1-M2. The second plot 220 illustrates the signal voltage across R1-R2. The third plot 230 illustrates the signal voltage V3. While the particular signals depicted in plots 200 are exemplary, any of the electrodes in the ECG may be depicted including RA (right arm), LA (left arm), RL (right leg), LL (left leg), V1 (fourth intercostal space), V2 (fourth intercostal space), V3 (between leads V2 and V4), V4 (fifth intercostal space), V5 (left anterior axillary line) and V6 (midaxillary line). The indication 240 of the signals is provided adjacent to the respective plot 200.

As illustrated, the voltage levels plotted in the y-axis may be varied in order to highlight, make them viewable on the display, particular aspects of the signal. This may be changed by accessing the scale change 260. Such a change may allow a signal characteristic, such as the PQRST signal characteristic 212 to be examined and with greater visibility. For example, the depolarization of the atria may be examined in the p-wave, the filling of the ventricles in the PR interval, the QRS complex and depolarization of the ventricles, the beginning of ventricle repolarization in the ST segment, and the T-wave ventricle repolarization.

In addition to the voltage level plot of height in the y-axis, which may be adjusted on a per plot level, the present system also includes an additional scale 250 for indicating global values to allow physicians to analyze the signal voltage based on the additional scale, such as color. Such a scale may enable comparisons across signals using the additional scale since the heights of the signals may be set differently to enable particular viewing on a feature, such as the PQRST for example. This scale 250 allows the analysis to be done faster and more accurately. Scale 250 allows for comparison across certain plots 210, 220, 230, for example, and is not dependent upon the voltage-level y-axis configuration. That is, scale 250 is not affected by scale change 260.

Physicians, or other users, may define the relevant threshold of scale 250 according to their preferences. In particular, the system may show signal strength in color and replace the color on the signal. Each signal 210, 220, 230 may be segmented into colors showing the signal strength for each segment of the signal. While the signal height may be modified for signal height changes in ones of the signals, in order to view portions of features of the respective signals, the displayed color scheme and colors of the signals are more absolute and do not change. This provides physicians and other personnel a better and faster method to analyze signals and compare between the signals via color.

In providing scale 250, any number of scaling systems may be used, including, but not limited to grayscale, other single color shade scales, multi-color scales, and the like. In providing scale 250, the positive and negative coloring may be designed to be symmetrical and the color changes from zero outward. Colors may be provided to be more apparent/clear/bright as the intensity increases. Other modifications may allow the user to decide if they want to change the color (hue) or just its brightness or saturation and to allow analysis of the signals more efficiently even by color deficient users, who often can view the brightness/saturation differences.

Figure 3:
FIG. 3 illustrates a depiction of a display screen of the device of FIG. 1.

FIG. 3 illustrates a depiction of a display screen 300 of the present invention. A first plot 310 illustrates the signal voltage across M1-M2. The second plot 320 illustrates the signal voltage across R1-R2. Other plots are also contemplated within the present invention and the two plots 310, 320 are illustrative only. As illustrated, the voltage levels plotted in the y-axis may be varied in order to highlight plots or certain aspects or otherwise make them viewable on the display. The scale may be changed by accessing the scale change 360. Such a change may allow a signal characteristic, such as the PQRST signal characteristic 312.

In addition to the voltage level plot of height in the y-axis, which may be adjusted on a per plot level, the present system also includes an additional scale 350 for indicating global values of signal level. Scale 350 allows for comparison across certain plots 310, 320, for example, and is not dependent upon the voltage-level of the y-axis configuration.

Scale 370 represents another color scale that is related to the map. This scale 370 may be provided for a different purpose than scale 350. Scale 370 provides a scale for the LAT value. Further, scale 370 provides information with portion of display 380. A three-dimensional depiction of the chamber walls of the heart are displayed and related to the ECG measurements. This 3-D depiction includes a representation of the catheters that are in the heart chambers at this point in time. This 3-D depiction provides an image of the heart chamber being mapped. This depiction provides context for the plots 310, 320, for example.

Figure 4:
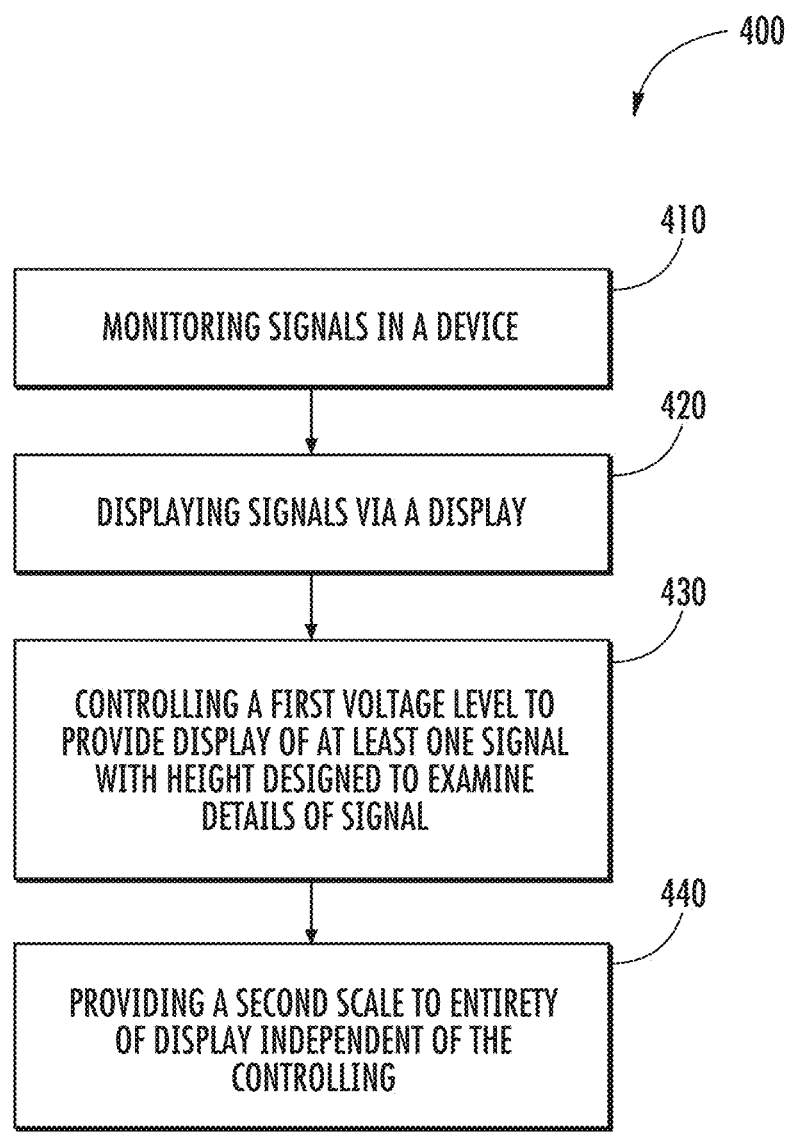
FIG. 4 illustrates a method of display for the device of FIG. 1.

FIG. 4 illustrates a method 400 of display for the device of FIG. 1. Method 400 includes the step of monitoring signals in a device at step 410. At step 420, method 400 includes displaying signals obtained via the device on a display. At step 430, method 400 includes controlling a first voltage display level to provide display of at least one measured signal with a height designed to examine details of the measured signal. Method 400 includes providing a second scale to the entirety of the display independent of the first voltage display level, at step 440.

Although features and elements are described above in particular combinations, one of ordinary skill in the art will appreciate that each feature or element can be used alone or in any combination with or without the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method of display of a plurality of measured signals in an electro cardiograph (ECG) device, the method comprising:
   monitoring the plurality of signals;
   displaying signals on a first display, the signals being at least a subset of the monitored signals;
   controlling a first voltage display level of the first display to provide display of at least one displayed measured signal with a height designed to examine details of the at least one displayed measured signal, the controlled first voltage display level of the at least one displayed measured signal being different from a voltage display of others of the at least one displayed measured signal; and
   providing a second scale to the entirety of the plurality of signals displayed on the first display, the second scale being independent of the first voltage display level.

2. The method of claim 1 wherein the second scale is provided in color.

3. The method of claim 1 wherein the first voltage display level is modified for at least one of the measured signals.

4. The method of claim 1 wherein modification of the first voltage display level does not affect the second scale.

5. The method of claim 1 wherein modification of the first voltage display level allows for examination of details of the signals.

6. The method of claim 1 wherein the second scale allows for interpretation of signal voltage levels absolutely.

7. The method of claim 6 wherein the second scale is based on color.

8. The method of claim 6 wherein the second scale is based on a secondary mechanism.

9. A display for a plurality of measured signals in an electro cardiograph (ECG), the display comprising:
   displaying the plurality of measured signals on a first display of the ECG by controlling a first voltage display level to provide display of at least one of the plurality of displayed measured signals with a height designed to examine details of the at least one of the plurality of displayed measured signals, the controlled first voltage display level of the at least one of the plurality of displayed measured signals being different from a voltage display of others of the at least one of the plurality of displayed measured signals; and
   providing a second scale to the entirety of the plurality of displayed measured signals independent of the first voltage display level on the first display.

10. The display of claim 9 wherein the second scale is provided in color.

11. The display of claim 9 wherein the first voltage display level is modified for at least one of the measured signals.

12. The display of claim 9 wherein modification of the first voltage display level does not affect the second scale.

13. The display of claim 9 wherein modification of the first voltage display level allows for examination of details of the signals.

14. The display of claim 9 wherein the second scale allows for interpretation of signal voltage levels absolutely.

15. The display of claim 14 wherein the second scale is based on color.

16. The display of claim 14 wherein the second scale is based on a secondary mechanism.

17. A device for measuring signal of interest, the device comprising:
   signal monitors for monitoring at least one signal within the device;
   a display for displaying signals on a display, the signals being at least a subset of the monitored signals;
   controlling a first voltage display level to provide the first display of at least one displayed measured signal with a height designed to examine details of the measured signal, the controlled first voltage display level of the at least one displayed measured signal being different from a voltage display of others of the at least one displayed measured signal; and
   providing a second scale to the first display and to the entirety of the signals displayed independent of the first voltage display level.

18. The device of claim 17 wherein modification of the first voltage display level does not affect the second scale.

19. The device of claim 17 wherein the second scale allows for interpretation of signal voltage levels absolutely.

20. The device of claim 19 wherein the second scale is based on color.

* * * * *